(12) United States Patent
Morgan et al.

(10) Patent No.: US 7,967,785 B2
(45) Date of Patent: Jun. 28, 2011

(54) INSULIN RESERVOIR DETECTION VIA MAGNETIC SWITCHING

(75) Inventors: Roy E Morgan, Weston, FL (US); Victor M Gamez, Fort Lauderdale, FL (US)

(73) Assignee: Nipro Healthcare Systems, LLC, Ft. Lauderdale, FL (US)

( * ) Notice: Subject to any disclaimer, the term of this patent is extended or adjusted under 35 U.S.C. 154(b) by 240 days.

(21) Appl. No.: 12/172,546

(22) Filed: Jul. 14, 2008

(65) Prior Publication Data
US 2010/0010443 A1    Jan. 14, 2010

(51) Int. Cl.
*A61M 1/00* (2006.01)
(52) U.S. Cl. .......................................... 604/151; 604/65
(58) Field of Classification Search ............... 417/477.2; 600/431–435; 604/65–67, 118–121, 132–147, 604/151–155, 890.1–892.1
See application file for complete search history.

(56) References Cited

U.S. PATENT DOCUMENTS

| | | | |
|---|---|---|---|
| 4,576,726 A * | 3/1986 | Watanabe et al. | 252/62.54 |
| 6,740,059 B2 | 5/2004 | Flaherty | |
| 6,743,202 B2 | 6/2004 | Hirschman et al. | |
| 6,817,986 B2 * | 11/2004 | Slate et al. | 604/68 |
| 7,041,082 B2 | 5/2006 | Blomquist et al. | |
| 7,104,767 B2 * | 9/2006 | Lee | 417/413.1 |
| 7,137,964 B2 | 11/2006 | Flaherty | |
| 7,273,477 B2 | 9/2007 | Spohn et al. | |
| 7,347,836 B2 | 3/2008 | Peterson et al. | |
| 7,353,688 B2 | 4/2008 | Harazin et al. | |
| 2005/0182358 A1 * | 8/2005 | Veit et al. | 604/93.01 |
| 2006/0106347 A1 * | 5/2006 | Fago et al. | 604/154 |
| 2007/0066940 A1 * | 3/2007 | Karunaratne et al. | 604/152 |
| 2007/0093752 A1 * | 4/2007 | Zhao et al. | 604/131 |
| 2008/0045904 A1 * | 2/2008 | Estes et al. | 604/152 |
| 2008/0135725 A1 * | 6/2008 | Bisch et al. | 250/206 |

OTHER PUBLICATIONS

International Search Report and Written Opinion dated Sep. 1, 2009 for International Application No. PCT/US2009/050503, International Filing Date Jul. 14, 2009 consisting of 8 pages.

* cited by examiner

*Primary Examiner* — Nicholas D Lucchesi
*Assistant Examiner* — Gerald Landry, II
(74) *Attorney, Agent, or Firm* — Finnegan, Henderson, Farabow, Garrett & Dunner, L.L.P.

(57) ABSTRACT

A system and method for detecting the presence of a medicament reservoir within the housing of an infusion pump. A medicament reservoir, affixed to a reservoir cap is removably inserted within the housing of an infusion pump. A magnet is affixed to or embedded in one or both of the reservoir or the reservoir cap. Alternately, the cap or the reservoir can be made of magnetic material. A sensing device embedded or otherwise affixed to the pump housing senses the presence or absence of the magnetic field created by the magnet. The presence of the magnetic field indicates that the reservoir is inserted properly within the housing and the absence of the magnetic field indicates that the reservoir has been at least partially withdrawn from the pump's housing.

19 Claims, 6 Drawing Sheets

US 7,967,785 B2

INSULIN RESERVOIR DETECTION VIA MAGNETIC SWITCHING

CROSS-REFERENCE TO RELATED APPLICATION

STATEMENT REGARDING FEDERALLY SPONSORED RESEARCH OR DEVELOPMENT n/a

FIELD OF THE INVENTION

The present invention relates to insulin pumps and more specifically to a method and system for detecting the presence of an insulin reservoir in an insulin pump using magnetic sensing and switching.

BACKGROUND OF THE INVENTION

Insulin pump systems allow patients to administer safe doses of an intravenous or subcutaneous medication at will, without the need for constant supervision by medical staff. These devices often include a pump housing that houses a cartridge, a motor, a drive system, and a power supply, which supplies power to the motor. The outside of the housing provides key pad entry for allowing the patient to program the rate of insulin delivery and to modify the delivery rate according to the patient's expected or actual carbohydrate intake. Many insulin pumps include a syringe having an insulin reservoir for the delivery of insulin into the patient's body.

The detection of the presence of containers that provide for insulin within the insulin reservoir is a critical functionality for the prevention of accidental injection of insulin during pump manipulation by the patient. In insulin pumps that have reciprocating injection mechanisms, it is required to position the pump injection piston according to the volume of insulin residing in the reservoir being loaded. If the patient instructs the pump to move its injection piston forward at high speed with a filled insulin reservoir still installed within the pump, an accidental injection of insulin may occur. Accidental insulin overdoses may result in severe hypoglycemia, a condition that may have fatal consequences. The ability to detect insulin reservoir presence in a pump may also be beneficial in other instances during pump operation.

Current infusion pump technology utilizes mechanical switches that require mechanical sealing to prevent the ingress of fluid. Since insulin pumps are often used during activities that involve immersion in water such as bathing and swimming, pumps that use such mechanical switching designs are prone to fluid ingress and are often failure points in pumps having these types of mechanical designs.

Given the inadequacies of the prior art techniques used to detect the present of insulin in the insulin reservoir, it would be desirable to provide a method and system that utilizes a non-mechanical design to detect the presence of insulin in the pump's insulin reservoir that does not require a break in the hermetically sealed enclosure of the pump.

SUMMARY OF THE INVENTION

The present invention advantageously provides a method and system for detecting the presence of a medicament reservoir, such as the barrel of an insulin syringe, within the housing of an infusion pump, via the use of a magnetic field source and a sensor calibrated to detect the presence or absence of a magnetic field created by the magnetic field source.

In one aspect of the invention, an infusion pump system for detecting the presence of a medicament container in an infusion pump is provided. The system includes a pump housing, a magnetically activated sensor located within the housing, a medicament container containing the medicament, where the medicament container is removably situated within the pump housing, and a magnetic field source for creating a magnetic field. When the sensor detects the presence of the magnetic field, this indicates that the medicament container is within the pump housing.

In another aspect of the invention, a method for detecting the presence of a medicament container in an infusion pump is provided. The method includes the steps of positioning a medicament container containing a medicament within an infusion pump housing, generating a magnetic field where the magnetic field is created by a magnetic field source and the magnetic source is positioned proximate the medicament container, and sensing the presence or absence of the magnetic field, wherein sensing the presence of the magnetic field indicates that the medicament container is within the infusion pump housing and sensing the absence of the magnetic field indicates that the medicament container is not within the infusion pump housing.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
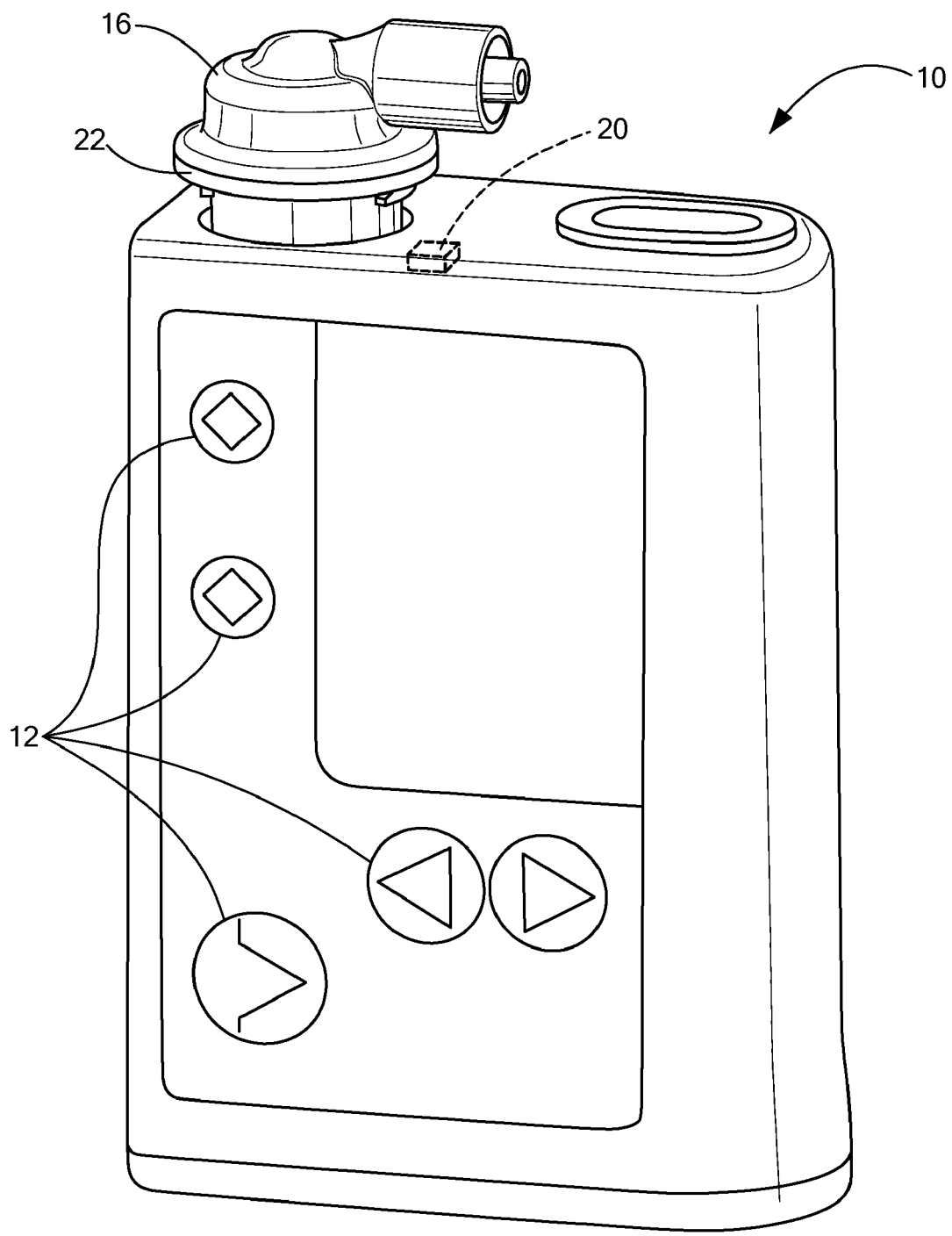
FIG. 1 is a front perspective view of an infusion pump in accordance with the principles of the present invention.

The present invention advantageously provides a method and system for detecting the presence of a medicament reservoir within the housing of an infusion pump. Referring now to the drawing figures in which like reference designators refer to like elements there is shown in FIG. 1 an infusion pump housing 10. Housing 10, which can be designed to fit conveniently in the pocket of a user or to be attached to a belt clip, receives a removable and disposable medicament container 14 (not shown in FIG. 1). Medicament container 14 could be, for example, the barrel of a medicament-dispensing syringe. The syringe barrel 14 holds a supply of a medicament, such as insulin, for injection into a diabetic person, or other user in need of the medicament. Barrel 14 is covered by head portion or cap 16 which seals the opening in barrel 14 via use of a locking mechanism such as a luer connection. An infusion set (not shown) can be affixed to the cap 16 in order to dispense insulin to the patient. When not affixed to an infusion set, a cap plug 18 can be used to cover the opening in cap 16. In FIG. 1, syringe barrel 14 is fully inserted within housing 10. In this orientation, insulin can be dispensed to the patient. Housing 10 includes buttons 12 for controlling the dispensing of insulin from the infusion pump, and a motor and a drive system for incrementally advancing a piston to eject the medicament from barrel 14. The motor is under the control of a processor, which is preferably housed within the housing 10.

It is often necessary for the patient to adjust the position of a pump injection piston within the barrel 14 according to the volume of insulin residing in the reservoir being loaded. During these instances, the patient does not want any insulin to be dispensed from the reservoir. However, during this time, the patient may inadvertently instruct the pump to move the injection piston forward with a filled insulin reservoir still installed within the pump. This might result in an accidental injection of insulin. Advantageously, the present invention allows the infusion pump to detect when the barrel 14 containing the insulin reservoir has been removed from the pump housing 10 by use of a sensing device 20 embedded within or affixed to housing 10, as shown in FIG. 1, and a magnetic field source 22 that establishes a magnetic field within the detection range of sensing device 20. In one embodiment, shown in FIG. 1, magnet 22 is formed as a gasket-like ring around cap 16. As discussed below, the invention is not limited to a specific location of magnet 22 or sensing device 20.

Sensing device 20 can be any device capable of detecting the presence or absence of a magnetic field within a certain range. Depending upon the action distance of sensing device 20, device 20 can be positioned at any of various locations within or on housing 10. The magnetic field triggers the sensing device 20 to send a signal that is recognized by the processor system within the pump, indicating the presence of a magnetic field. The processor interprets the detection of a magnetic field as indicating that the insulin reservoir within syringe barrel 14 is properly engaged in the infusion pump. If sensing device 20 detects the absence of the magnetic field, a signal is generated and interpreted by the pump's processor as indicating that the insulin reservoir is not properly engaged within housing 10 of the infusion pump. A warning signal can be generated to inform the patient that the insulin reservoir is not properly situated within the pump. More than one sensing device 20 can also be positioned at various locations within housing 10 in order to detect the presence of the magnetic field. Similarly, more than one magnetic field source 22 can be used and placed on or within various locations such as but not limited to the syringe barrel 14 or cap 16.

Sensing device 20 need not be positioned within the pump at the location indicated in FIG. 1. As discussed above, sensing device 20 can be located virtually anywhere within or on housing 10 of the pump, depending upon its action distance, i.e., the furthest distance that it is able to detect the presence of a magnetic field. Similarly, one or more magnets 22 can be located anywhere on cap 16 or on syringe barrel 14.

Figure 2:
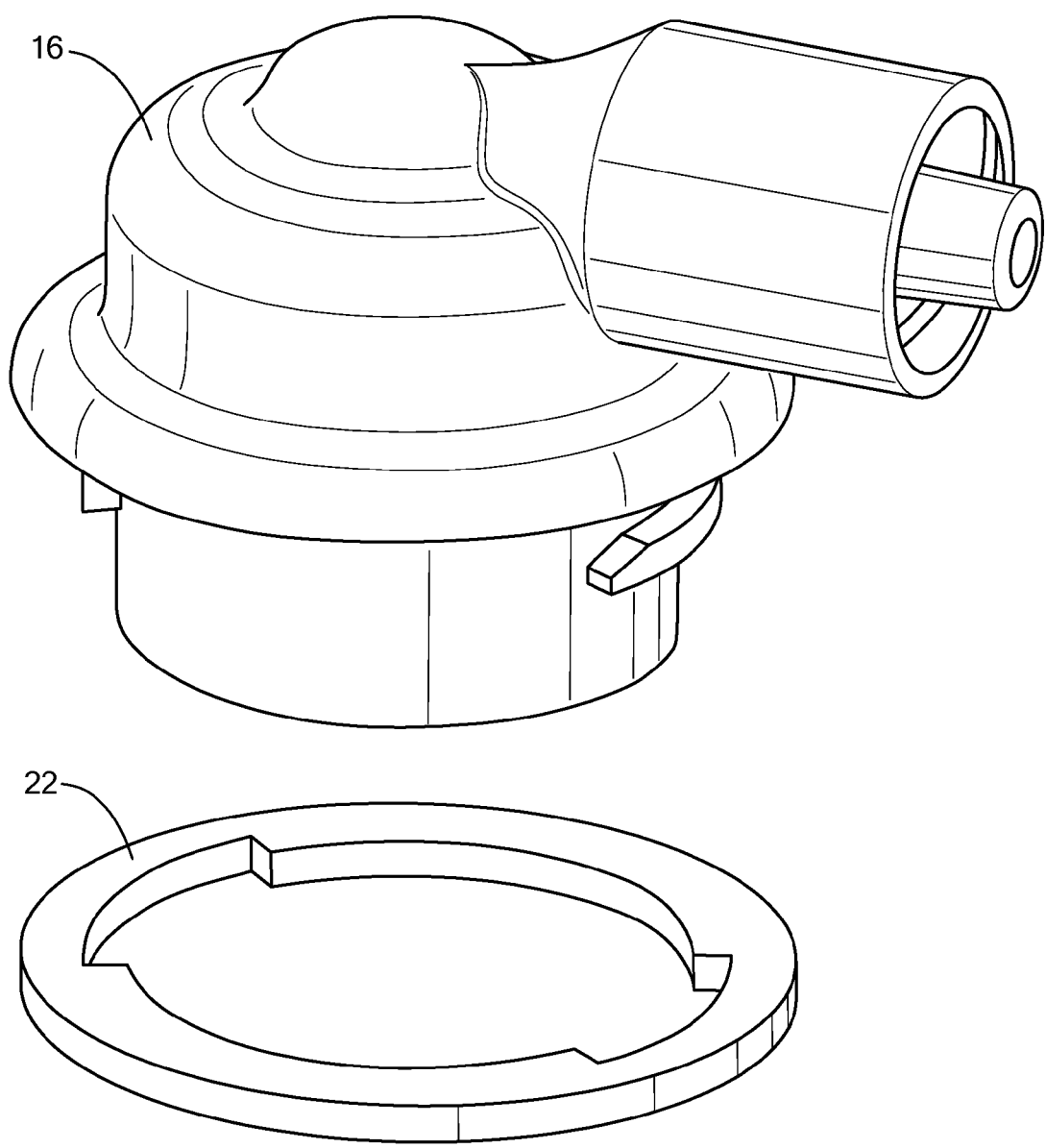
FIG. 2 is a perspective view of a syringe cap and gasket-like magnet in accordance with the principles of the present invention.

In the embodiment shown in FIG. 2, magnet 22 is substantially circular and is sized to fit around the outer circumference of cap 16, much like a gasket. Cap 16 is secured to syringe barrel 14, which contains the insulin reservoir, by a locking mechanism such as a luer connection. When the syringe barrel 14 containing the insulin reservoir is fully inserted within housing 10 of the pump, as shown in FIG. 1, sensing device 20 detects the presence of the magnetic field from magnet 22 and signals the pump's processor that a magnetic field is present, which indicates that the insulin reservoir is properly installed within the pump. Sensing device 20 can be calibrated to detect even the slight withdrawal of syringe barrel 14 from housing 10.

Figure 3:
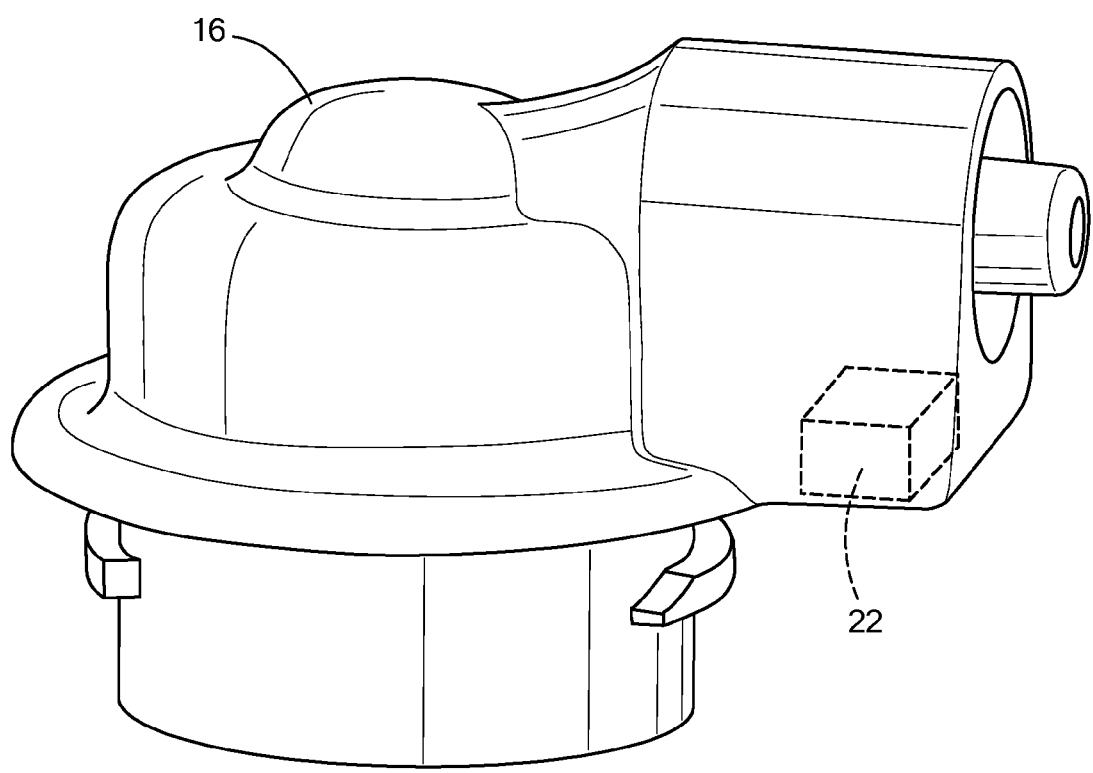
FIG. 3 is a perspective view of a syringe cap having an embedded magnet in accordance with the principles of the present invention.

FIG. 3 illustrates another embodiment of the present invention. In this embodiment, magnet 22 is embedded within the body of cap 16. Although shown in a particular location within cap 16, the present invention contemplates the placement of magnet 22 at any location within cap 16. Because of the attachment of cap 16 to syringe barrel 16, any withdrawal of syringe barrel 14 in a direction away from housing 10 also moves cap 16 in the same direction. Thus, depending on where magnet 22 is located on cap 16, sensing device 20 can be calibrated to detect when magnet 22 moves outside of the action range of device 20.

In yet another embodiment, the body of cap 16 can be made, at least partially, out of magnetic material or from material doped with a magnetic field source, or be made from magnetic inks that can provide sufficient magnetic field strength for sensing device 20.

Figure 4:
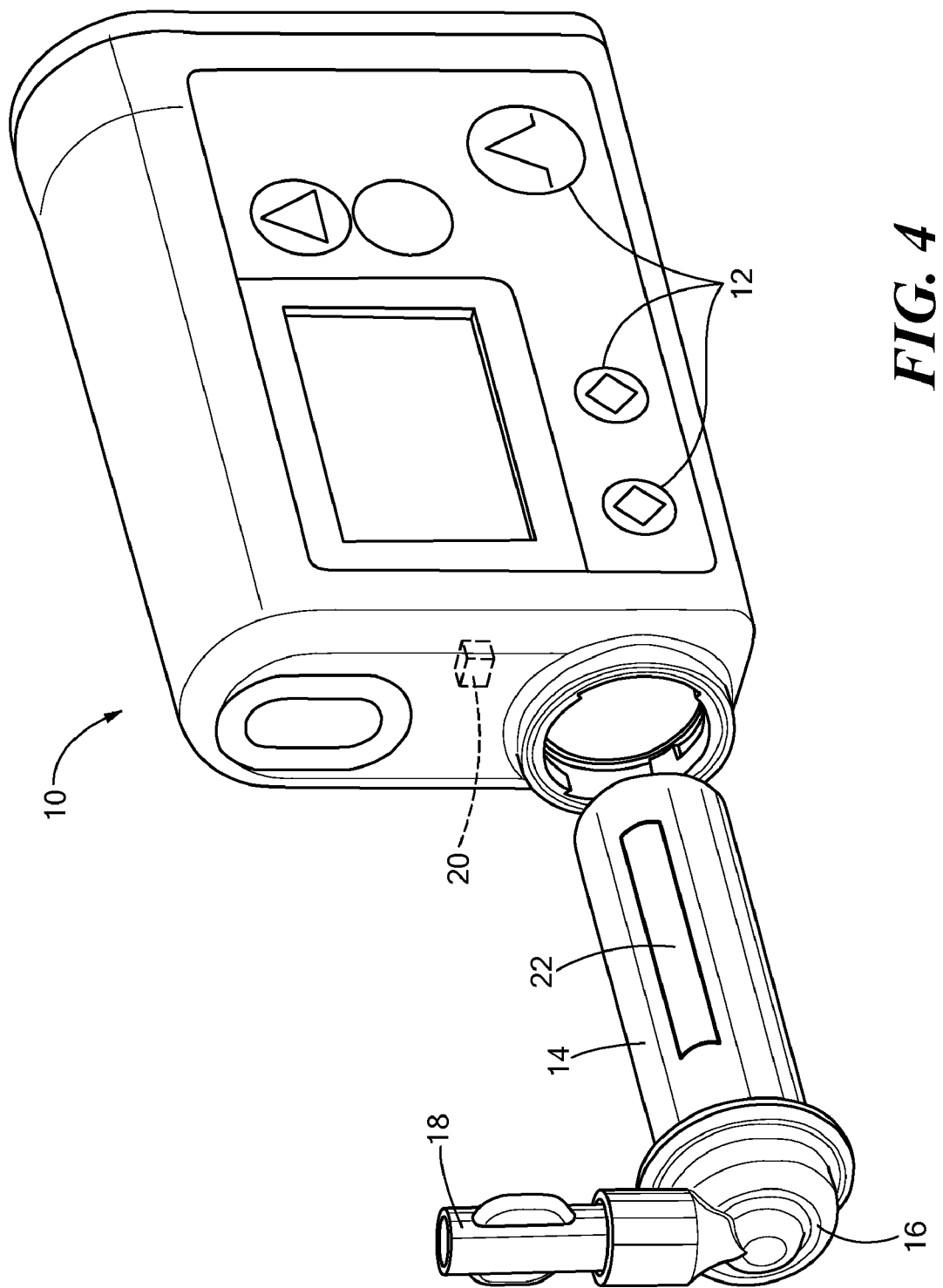
FIG. 4 is a front perspective view of an infusion pump with a removable syringe having an external magnet in accordance with the principles of the present invention.

The magnetic field source 22 need not be situated on or within cap 16. FIG. 4 shows syringe barrel 14 and cap 16 withdrawn from pump housing 10. In this embodiment, magnet 22 is affixed externally, in a longitudinal fashion, to syringe barrel 14. Sensing device 20 (not shown in FIG. 2) is calibrated to detect the presence and absence of the magnetic field when syringe barrel 14 is withdrawn from housing 10.

Figure 5:
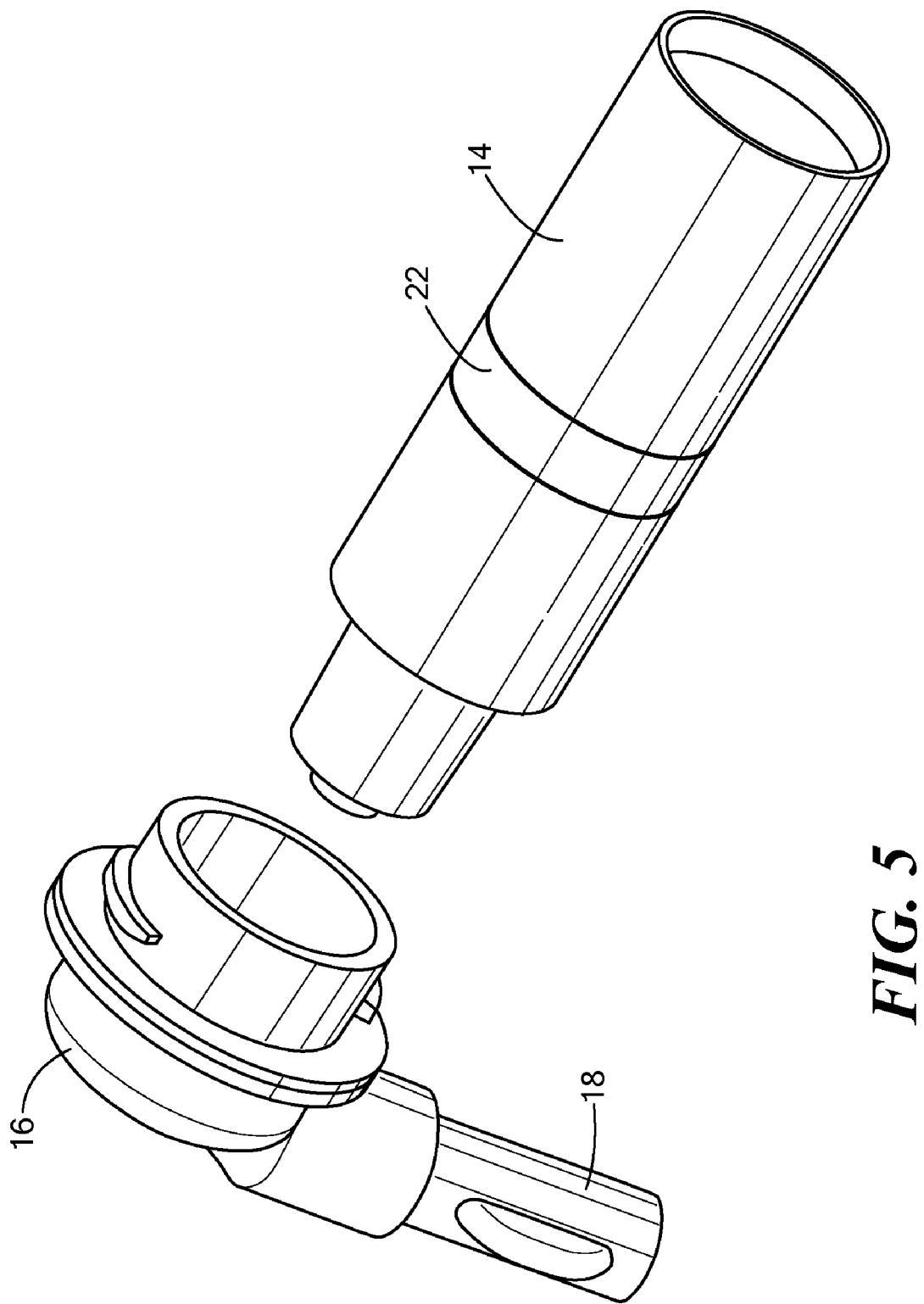
FIG. 5 is a perspective view of an alternate embodiment of the syringe having an external circumferential magnetic field source in accordance with the principles of the present invention.
Figure 6:
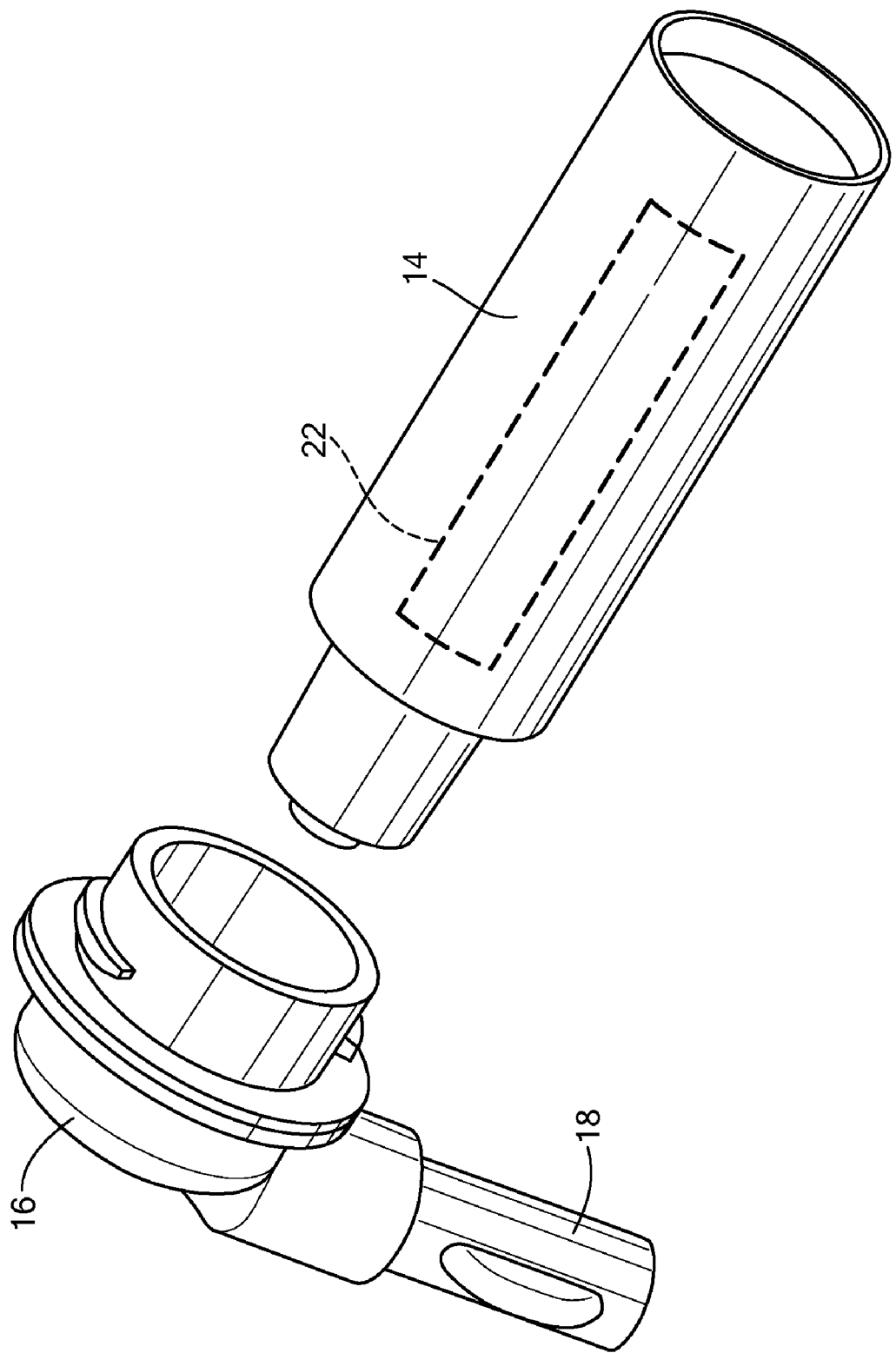
FIG. 6 is a perspective view of a syringe having an internal magnet in accordance with the principles of the present invention.

In another embodiment, magnet 22 can be disposed circumferentially around the outside of syringe barrel 14, as shown in FIG. 5 In yet another embodiment, magnet 22 can be disposed internally within syringe barrel 14, as shown in FIG. 6. Other embodiments of the present invention can include an insulin reservoir body such as syringe barrel 14 made from magnetic material or doped with a magnetic field source. Regardless of the location of magnet 22, sensing device 20 is situated somewhere on or in the infusion pump in order to be within detectable reach of the magnetic field created by the magnet 22. Sensing device 20 is in electrical communication with the pump's processor, or a remote processor. Sensing device 20 transmits electrical signals to the processor where they are interpreted to determine if the insulin reservoir is within the body of the pump or is not within the body of the pump.

The present invention is not limited to insulin reservoirs in the form of syringes. For example, the invention is equally adaptable to a pouch or container that houses insulin. As in the earlier described embodiments related to insulin syringes, magnetic field source 22 can be affixed to or embedded within the pouch.

The present invention advantageously provides a method and apparatus for detecting when a medicament reservoir is properly inserted within a medicament dispensing pump. The method and apparatus can further determine when the medicament reservoir is at least partially withdrawn from the housing of the medicament dispensing pump. One or more sensing devices 20 are embedded or otherwise affixed to the housing 10 of the dispensing pump. Sensing device 20 then detects the presence and the absence of a magnetic field and can be calibrated to increase of decrease its magnetic field detection range depending upon the needed requirements. One or more magnetic field sources 22 can be affixed to or embedded within a medicament reservoir 14 such as an insulin syringe. Alternately, the magnetic field source 22 can be embedded within or affixed to a cap 16 which is itself affixed to the medicament reservoir 14. Alternately, the cap 16 or the reservoir 14 can be made of magnetic material which creates the magnetic field.

Sensing device 20 is calibrated in such a way that it can detect the presence of the magnetic field when reservoir 14 is situated properly within housing 10. Device 20 sends a signal to the pump's processor indicating the presence of the magnetic field. The processor interprets this signal as meaning the medicament reservoir 14 is properly inserted in housing 10. When reservoir 14 is withdrawn from housing 10 of the medicament dispensing device, device 20 senses the absence of the magnetic field and sends a corresponding signal to the pump's processor. The processor interprets this signal as indicating that the reservoir 14 is not properly engaged within housing 10. The pump can then emit a warning signal, either audible, visual, or tactile, warning the user of the pump that the reservoir is not properly engaged within the housing 10 of the pump.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An infusion pump system comprising:
a pump housing;
a pump fixed in the pump housing;
a medicament container configured to be removably situated within the pump housing;
a magnetic field source associated with the medicament container; and
a magnetically activated sensor fixed within or on the pump housing and configured to detect the presence of the magnetic field source,
wherein the medicament container includes the magnetic field source and wherein the medicament container is doped with magnetic material.

2. The system of claim 1, wherein the sensor is configured to detect an absence of the magnetic field source indicating that the medicament container is at least partially withdrawn from the pump housing.

3. The system of claim 1, further comprising a processor configured to receive a signal from the magnetically activated sensor and to control actuation of the pump.

4. The system of claim 3, wherein the processor is configured to trigger a warning signal to be generated when the magnetically activated sensor indicates the medicament container is not situated within the pump housing.

5. The system of claim 3, wherein the processor is configured to limit actuation of the pump when the magnetically activated sensor indicates the medicament container is situated within the pump housing.

6. An infusion pump system comprising:
a pump housing;
a pump fixed in the pump housing;
a medicament container configured to be removably situated within the pump housing;
a magnetic field source associated with the medicament container; and
a magnetically activated sensor fixed within or on the pump housing and configured to detect the presence of the magnetic field source,
wherein the medicament container includes the magnetic field source, wherein the magnetic field source is externally affixed to the outside of the medicament container, and wherein the magnetic field source is circumferentially affixed to the medicament container.

7. The system of claim 6, wherein the sensor is configured to detect an absence of the magnetic field source indicating that the medicament container is at least partially withdrawn from the pump housing.

8. The system of claim 6, further comprising a processor configured to receive a signal from the magnetically activated sensor and to control actuation of the pump.

9. The system of claim 8, wherein the processor is configured to trigger a warning signal to be generated when the magnetically activated sensor indicates the medicament container is not situated within the pump housing.

10. The system of claim 8, wherein the processor is configured to limit actuation of the pump when the magnetically activated sensor indicates the medicament container is situated within the pump housing.

11. An infusion pump system comprising:
a pump housing;
a pump fixed in the pump housing;
a medicament container configured to be removably situated within the pump housing;
a magnetic field source associated with the medicament container; and
a magnetically activated sensor fixed within or on the pump housing and configured to detect the presence of the magnetic field source,
wherein the medicament container includes the magnetic field source, wherein the magnetic field source is externally affixed to the outside of the medicament container, and wherein the magnetic field source is longitudinally affixed to the outside of the medicament container.

12. The system of claim 11, wherein the sensor is configured to detect an absence of the magnetic field source indicating that the medicament container is at least partially withdrawn from the pump housing.

13. The system of claim 11, further comprising a processor configured to receive a signal from the magnetically activated sensor and to control actuation of the pump.

14. The system of claim 13, wherein the processor is configured to trigger a warning signal to be generated when the magnetically activated sensor indicates the medicament container is not situated within the pump housing.

15. The system of claim 13, wherein the processor is configured to limit actuation of the pump when the magnetically activated sensor indicates the medicament container is situated within the pump housing.

16. An infusion pump system comprising:
a pump housing;
a pump fixed in the pump housing;
a medicament container configured to be removably situated within the pump housing;
a magnetic field source associated with the medicament container;
a magnetically activated sensor fixed within or on the pump housing and configured to detect the presence of the magnetic field source; and
a cap affixed to the medicament container, the cap including the magnetic field source, wherein the magnetic field source is embedded within the cap.

17. The system of claim 16, wherein the cap is made of magnetic material.

18. The system of claim 16, wherein the sensor is configured to detect an absence of the magnetic field source indicating that the medicament container is at least partially withdrawn from the pump housing.

19. The system of claim 16, further comprising a processor configured to receive a signal from the magnetically activated sensor and to control actuation of the pump.

* * * * *